United States Patent [19]

Liu et al.

[11] 4,230,866

[45] Oct. 28, 1980

[54] PREPARATION OF 3-ARYL-ISOXAZOL-5-YL-BENZOIC ACID AND SALTS THEREOF

[75] Inventors: Kou-Chang Liu, Creve Coeur; Robert K. Howe, Bridgeton, both of Mo.

[73] Assignee: Monsanto Company, St. Louis, Mo.

[21] Appl. No.: 39,935

[22] Filed: May 17, 1979

[51] Int. Cl.$^3$ .......................................... C07D 261/08
[52] U.S. Cl. ................................................. 548/247
[58] Field of Search ................... 260/307 H; 548/247

[56] References Cited

U.S. PATENT DOCUMENTS

| | | | |
|---|---|---|---|
| 3,947,263 | 3/1976 | Brouwer et al. | 71/76 |
| 3,964,896 | 6/1976 | Brouwer et al. | 71/92 |
| 4,032,644 | 6/1977 | Nadelson | 424/272 |
| 4,135,910 | 1/1979 | Howe | 71/92 |
| 4,140,515 | 2/1979 | Howe | 71/88 |

FOREIGN PATENT DOCUMENTS 1494877  12/1977  United Kingdom ............... 260/307 H

*Primary Examiner*—Anton H. Sutto
*Attorney, Agent, or Firm*—Patricia A. Coburn; Donald W. Peterson

[57] ABSTRACT

3-Aryl-isoxazol-5-yl benzoic acid and salts thereof are prepared by base treatment of 3'-(Aryl)-spiro[isobenzofuran-1(3H),5'(4'H)-isoxazol]-3-one.

9 Claims, No Drawings

PREPARATION OF 3-ARYL-ISOXAZOL-5-YL-BENZOIC ACID AND SALTS THEREOF

This invention relates to the preparation of isoxazol5-yl benzoic acid salts that are useful in agriculture. Specifically, salts prepared in accordance with the present invention are salts of free acids which have the following structure.

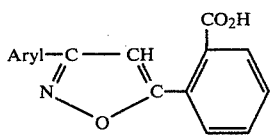

Belgian Pat. No. 837,454 discloses such compounds to be effective plant growth regulants. In addition, U.S. patent application Ser. No. 796,248, filed May 12, 1977, now abandoned, U.S. patent application Ser. No. 907,069, filed May 18, 1978, now abandoned, and U.S. patent application Ser. No. 966,403, filed Dec. 4, 1978, all of which are herewith incorporated by reference, disclose that such compounds are useful in regulating the growth of desirable plants as well as controlling the growth of undesirable plants. Said applications disclose that the isoxazol-5-yl benzoates are prepared by conversion of isoxazolin-5-yl benzoate with N-bromosuccinimide or dichlorodicyanobenzoquinone. Isoxazolin-5yl benzoates are prepared, however, from vinyl benzoates which are somewhat difficult to prepare.

In accordance with the novel aspects of the present invention, a salt of 3-aryl-isoxazol-5-yl benzoic acid is prepared by base treatment of 3'-(aryl)-spiro[isobenzofuran-1(3H),5'(4'H)-isoxazol]-3-one. 3-(Aryl)-spiro[isobenzofuran-1(3H),5'(4'H)-isoxazol]-3-ones have been disclosed in our co-pending application Ser. No. 971,462, filed Dec. 20, 1978, which is herewith incorporated by reference, and are prepared as disclosed therein by reaction of a nitrile oxide with 3-methylenephthalide in accordance with the following equation:

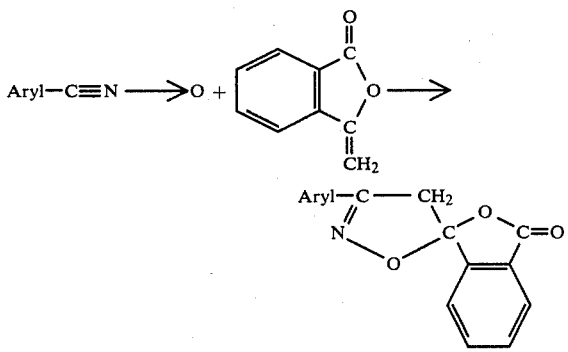

Since the Aryl radical takes no appreciable part in the reaction, any aromatic radical or heteroaromatic radical, e.g., pyridyl, may be used. Preferably, however, Aryl is a radical of the following formula wherein X and Y are independently selected from the group consisting of hydrogen, halogen, lower alkyl, lower alkoxy, halo-lower-alkyl, phenoxy, phenyl and cyano.

As used herein, the terms "lower alkyl" and "lower alkoxy" are understood to include those alkyl and alkoxy groups having up to five carbon atoms, inclusive. Both straight as well as branched chain alkyl groups are contemplated.

The term "halo-lower-alkyl" as used herein is understood to mean those lower alkyl groups in which at least one, and perhaps all, of the hydrogen atoms have been replaced by halogen atoms. It is to be clearly understood that trifluoromethyl is contemplated as being a halo-lower-alkyl moiety.

The term "halogen" as used herein includes chlorine, bromine, fluorine and iodine.

In accordance with the process of the invention, the spiro compound is mixed with a strong base resulting in a salt of 3-aryl-isoxazol-5-yl benzoic acid. Although a stoichiometric amount of base may be utilized it is preferable to dissolve the base in water and utilize a slight excess. Additional solvents have been found to enhance the reaction.

The reaction may be conducted at room temperature and atmospheric pressure. Although temperatures and pressures above ambient may be utilized, for obvious reasons ambient conditions are preferred.

The specific base used is not critical. However, the use of strong bases increases the rate of reaction. Generally, the base used should be of sufficient basicity to abstract the hydrogen from the 4-position of the isoxazoline ring. It is thought that a base having a $pK_A$ of 11 or more will be sufficient. This includes but is not limited to such bases as alkali metal hydroxides, alkaline earth hydroxides, alkali metal carbonates, aliphatic amines, etc.

If desired, the salt may be converted to the free acid by acidification. Additionally, the acid may be converted to an ester utilizing known procedures.

If a solvent is utilized the specific solvent used is not critical. It is desirable, however, to utilize a water-miscible solvent in order to enhance the reaction of the spiro compound with the base. This is especially true if an aqueous base is a reactant. Useful solvents include water, alcohol, dioxane, tetrahydrofuran, dimethylsulfide and the like.

In order to illustrate the novel aspects of the present invention, the following examples are presented. Said examples are presented for illustration and are not intended as a limitation with respect to the scope of the invention.

EXAMPLE 1

Preparation of 2-[3-o-Methylphenyl)-5-isoxazolyl]-benzoic acid.

To 3'-(o-methylphenyl)-spiro[isobenzofuran-1(3H),5'(4'H)-isoxazol]-3-one (2.5 g, 0.0085 mole) in 25 ml of ethanol was added a solution 0.6 g (0.015 mole) of sodium hydroxide in 25 ml of water. The solution was stirred for two hours. An additional 50 ml of water was added and stirring continued resulting in a solution containing a salt of the desired acid. The solution was then acidified with concentrated hydrochloric acid and extracted with 200 ml of ether. The ethereal solution was washed two times with water, dried over calcium sulfate and concentrated under a vacuum to give 2.40 g of the desired acid as white crystals, mp. 158.5°–159.5° C. The crystals were recrystallized from 10 ml of acetonitrile to give 1.55 g of colorless crystals, mp 160.5°–161.5° C.

Anal. Calc'd: C,73.11; H,4.69. Found: C,73.08; H,4.71.

EXAMPLE 2

Preparation of 2-[3-(m-Trifluoromethylphenyl)-5-isoxazolyl]benzoic acid.

To 1.0 g of 3'-(m-trifluoromethylphenyl)-spiro [isobenzofuran-1(3H),5'(4'H)-isoxazol]-3-one dissolved in 25 ml of ethanol was added 20 ml of a 1 N sodium hydroxide solution. The solution was stirred at room temperature for five hours giving the sodium salt of the desired acid. The clear solution was acidified with concentrated hydrochloric acid, extracted with 300 ml of ether, washed two times with water, dried over calcium sulfate and concentrated to give 0.98 g of the desired acid as a white solid, mp 175°–176° C.

EXAMPLE 3

Preparation of 2-[3-(m-Cyanophenyl)-5-isoxazolyl]-benzoic acid.

Utilizing the procedure of Example 1, 2-[3-(m-cyanophenyl)-5-isoxazolyl]benzoic acid, mp 195°–196° C., was prepared.

Anal. Calc'd: C,70.34; H,3.47. Found: C,70.22; H,3.49.

The above examples disclose an efficient process for preparing 3-aryl-isoxazol-5-yl benzoic acids and salts thereof that are useful as herbicides and plant growth regulants. If desired, the acid may be esterified resulting in additional herbicides and plant growth regulants.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for preparing a salt of 3-Aryl-isoxazol-5-yl-benzoic acid which comprises reacting a spiro compound having the formula

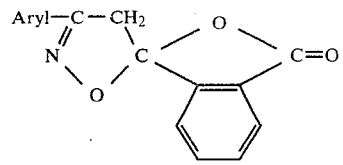

with a base having a pK$_A$ of 11 or more, in the presence of a water-miscible solvent.

2. A process according to claim 1 wherein said base is selected from the group consisting of alkali metal hydroxides, alkaline earth carbonates, alkali metal carbonates and aliphatic amines.

3. A process according to claim 1 wherein said Aryl is

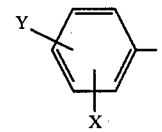

wherein X and Y are independently selected from the group consisting of hydrogen, halogen, lower alkyl, lower alkoxy, halo-lower alkyl, phenoxy, phenyl and cyano.

4. A process according to claim 3 wherein X is hydrogen and Y is halo-lower alkyl.

5. A process according to claim 4 wherein said spiro compound has the formula

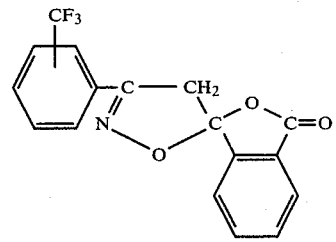

6. A process according to claim 5 wherein said trifluoromethyl moiety is in the meta position.

7. A process according to claim 6 wherein said base is an alkali metal hydroxide.

8. A process according to claim 7 which comprises reacting a spiro compound having the formula

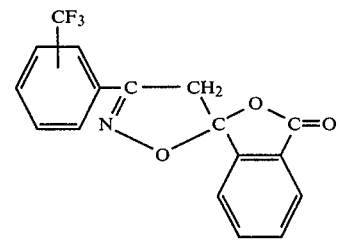

with sodium hydroxide in the presence of an alcohol.

9. A process according to claim 1 further comprising the step of reacting the salt produced by the process of claim 1 with an acid to form the free acid of said salt.

* * * * *